United States Patent [19]

Doria et al.

[11] 4,310,589

[45] * Jan. 12, 1982

[54] 2-(PYRIDYL-CYCLOPROPYL)CHROMONES

[75] Inventors: Gianfederico Doria, Milan; Ciriaco Romeo, Serino; Maria L. Corno, Milan; Piero Sberze, Varese; Marcellino Tibolla, Canale d'Agordo, all of Italy

[73] Assignee: Farmitalia Carlo Erba S.p.A., Milan, Italy

[*] Notice: The portion of the term of this patent subsequent to Jul. 3, 1996, has been disclaimed.

[21] Appl. No.: 186,544

[22] Filed: Sep. 12, 1980

[30] Foreign Application Priority Data

Oct. 26, 1979 [GB] United Kingdom ............... 37200/79

[51] Int. Cl.$^3$ ................. C07D 405/08; A61K 31/395
[52] U.S. Cl. ..................................... 424/263; 546/269
[58] Field of Search ......................... 546/269; 424/263

[56] References Cited

U.S. PATENT DOCUMENTS

| | | | |
|---|---|---|---|
| 3,816,466 | 6/1974 | von Strandtmann et al. ... | 260/345.2 |
| 3,896,114 | 7/1975 | Nohara et al. ................. | 260/240 E |
| 3,993,669 | 11/1976 | Pfister .............................. | 260/345.2 |
| 4,018,798 | 4/1977 | Cohen et al. ..................... | 260/345.2 |
| 4,033,845 | 7/1977 | Cohen et al. ..................... | 260/240 D |
| 4,143,145 | 3/1979 | Doria et al. ........................ | 424/263 |
| 4,152,449 | 5/1979 | Doria et al. ........................ | 424/283 |
| 4,157,334 | 6/1979 | Doria et al. ..................... | 260/345.2 |
| 4,160,028 | 7/1979 | Doria et al. ..................... | 424/248.51 |

FOREIGN PATENT DOCUMENTS 781467 3/1968 Canada .

OTHER PUBLICATIONS

Shah et al., *J. Chem. Soc.*, pp. 2663–2666 (1961).
Renzi, et al., *Chemical Abstracts*, vol. 67, entry 64296 (1967).
Koo, *J. Org. Chem.*, vol. 26, pp. 2440–2442 (1961).
Belgium Abstract 844,884, 844,943 Feb. 1977.

*Primary Examiner*—John M. Ford
*Attorney, Agent, or Firm*—Murray and Whisenhunt

[57] ABSTRACT

The present invention relates to substituted 2-(pyridyl-cyclopropyl)-chromones, to a process for their preparation and to pharmaceutical compositions containing them.

12 Claims, No Drawings

2-(PYRIDYL-CYCLOPROPYL)CHROMONES

The present invention relates to substituted 2-(pyridyl-cyclopropyl)-chromones, to a process for their preparation and to pharmaceutical compositions containing them.

The invention provides compounds having the following general formula (I)

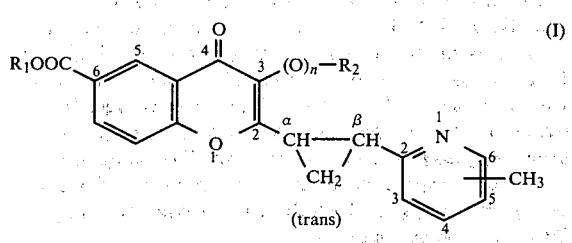

wherein
n is 0 or 1;
$R_1$ represents a hydrogen atom or a $C_1$-$C_4$ alkyl group which is unsubstituted or substituted by a

group, wherein each of $R_3$ and $R_4$ independently represents a hydrogen atom or a $C_1$-$C_2$ alkyl group;
$R_2$ represents a $C_2$-$C_3$ alkyl group or an allyl group and wherein the methyl group on the pyridine ring is in the 6- or in the 5-position, preferably the methyl group on the pyridine ring is in the 6-position.

The compounds of the invention include also the pharmaceutically acceptable salts of the compounds of formula (I).

The compounds of the invention are in the trans configuration, that is the two hydrogen atoms on the α and the β carbon atoms are on opposite sides in respect of the plane of the cyclopropane ring.

Examples of pharmaceutically acceptable salts are those with inorganic bases, such as sodium, potassium, calcium and aluminium hydroxides or with organic bases, such as lysine, triethylamine, triethanolamine, dibenzylamine, methylbenzylamine, di-(2-ethyl-hexyl)-amine, piperidine, N-ethylpiperidine, N,N-diethylaminoethylamine, N-ethylmorpholine, β-ethylmorpholine, β-phenethylamine, N-benzyl-β-phenethylamine, N-benzyl-N,N-dimethylamine and the other acceptable organic amines, as well as the salts with inorganic, e.g. hydrochloric, hydrobromic and sulphuric acids and with organic acids, e.g. citric, tartaric, maleic, malic, fumaric, mathanesulphonic and ethanesulphonic acids. Preferred salts are the sodium and the potassium salts, as well as the hydrochlorides of the basic esters, e.g. the preferred diethylaminoethyl and dimethylaminoethyl esters. Particularly preferred compounds of the invention are those of formula (I) wherein the —COOR₁ group is a free or salified carboxy group and the methyl group on the pyridine ring is in the 6 position.

Examples of particularly preferred compounds of the invention are:

2-trans-[2-(6-methyl-2-pyridyl)-cyclopropyl]-3-propyl-chromone-6-carboxylic-acid 2-trans-[2-(6-methyl-2-pyridyl)-cyclopropyl]-3-propoxy-chromone-6-carboxylic-acid 2-trans-[2-(6-methyl-2-pyridyl)-cyclopropyl]-3-ethoxy-chromone-6-carboxylic-acid 2-trans-[2-(6-methyl-2-pyridyl)-cyclopropyl]-3-allyloxy-chromone-6-carboxylic acid 2-trans-[2-(5-methyl-2-pyridyl)-cyclopropyl]-3-propyl-chromone-6-carboxylic-acid 2-trans-[2-(6-methyl-2-pyridyl)-cyclopropyl]-3-propyl-chromone-6-carboxylic-acid, 2-diethylamino-ethyl ester, as well the pharmaceutically acceptable salts thereof, in particular the sodium salts and the hydrochlorides of the basic esters (e.g. those with 2-diethylamino-ethanol and 2-dimethylamino-ethanol).

The compounds of the invention may be prepared for example, by reacting a compound of formula (II)

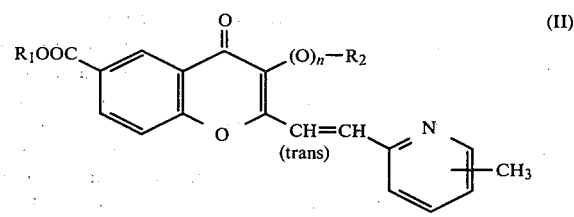

wherein n, $R_1$ and $R_2$ are as defined above, and wherein the methyl group on the pyridine ring is in the 6-or in the 5-position, with dimethylsulphoxonium methylide and/or, if desired, converting a compound of formula (I) into another compound of formula (I) and/or, if desired, converting a compound of formula (I) into a pharmaceutically acceptable salt thereof and/or, if desired, converting a salt into a free base or acid. The reaction of a compound of formula (II) with dimethylsulphoxonium methylide (that is the compound (CH₃)₂

prepared, e.g., according to the method described in J. Chem. Soc., 1967,2495) is preferably carried out in an inert organic solvent selected e.g. from the group consisting of dimethylformamide, dimethylsulphoxide dioxane and their mixtures, at a temperature ranging preferably between about 0° C. and about 50° C.

A compound of formula (I) may be converted, as stated above, into another compound of formula (I) by known methods; for example, the compound of formula (I) wherein —COOR₁ is an esterified carboxy group, may be converted into a compound of formula (I) wherein —COOR₁ is carboxy by hydrolysis, e.g. basic hydrolysis, using, for example, sodium or potassium hydroxide, in a solvent, e.g. water or a lower aliphatic alcohol, and operating at a temperature ranging from the room temperature to about 150° C; the same reaction may be also carried out e.g. by treatment with lithium bromide in dimethylformamide at a temperature higher than 50° C.

Also, a compound of formula (I) wherein —COOR₁ is a t-butoxycarbonyl group may be converted into a compound of formula (I) wherein —COOR₁ is carboxy e.g. by treatment with trifluoroacetic acid either in the absence of solvents or in the presence of an inert organic solvent selected e.g. from the group consisting of benzene, toluene, dioxane at a temperature ranging from about 0° C. to about 50° C. or also by treatment, e.g. with trimethylsilyliodide in an inert organic solvent, preferably tetrachloromethane, according to the procedure described in J.Am.Chem. Soc. 99, 968 (1977).

A compound of formula (I) wherein —COOR$_1$ is carboxy may be converted into a compound of formula (I) wherein —COOR$_1$ is a C$_2$-C$_5$ carbalkoxy group unsubstituted or substituted by a

group, wherein R$_3$ and R$_4$ are as defined above, by conventional methods, for example by reacting the alkali metal salt of the acid with the alkyl halide, in an inert solvent, e.g., acetone, dioxane, dimethylformamide, hexamethylphosphorotriamide at a temperature ranging from about 0° C. to about 100° C. Alternatively the esterification of a compound of formula (I) may be effected (a) converting the compound of formula (I) wherein —COOR$_1$ is carboxy into the corresponding halocarbonyl, preferably chlorocarbonyl, derivative, by reaction, e.g., with the desired acid halide, for example oxalyl chloride, thionyl chloride, PCl$_3$, PCl$_5$ or POCl$_3$, either in the absence of solvents or in an inert organic solvent e.g. benzene, toluene, xylene, dioxane, dichloroethane, methylene chloride, tetrahydrofurane, at a temperature ranging preferably from about 0° C. to about 120° C., and then (b) reacting the obtained halocarbonyl derivative with an alcohol of formula R$_1$—OH, wherein R$_1$ is as defined above, in an inert solvent e.g. benzene, toluene, xylene, dioxane, dichloroethane, methylene chloride, tetrahydrofurane, at temperatures varying between about 0° C. and about 120° C., preferably in the presence of a base, e.g. triethylamine or diethylamine.

Also the optional salification of a compound of formula (I) as well as the conversion of a salt into the free compound may be carried out by conventional methods.

The compounds of formula (II) may be prepared, for example, according to the methods described in our U.S. Pat. Nos. 4,143,145 and 4,177,276.

The compounds of the invention have antiallergic activity and are therefore useful in the prevention and treatment of all affections of allergic origin, e.g., bronchial asthma, allergic rhinitis, hay fever, urticaria and dermatosis. The antiallergic activity of the compounds of the invention is shown, e.g., by the fact that they are active in the rat in the passive cutaneous anaphylaxis (PCA) test of J. Goose and A.M.I.N. Blair (Immunology 16, 749, 1969).

An important property of the compounds of the invention is that they exhibit a high level of antiallergic activity when administered orally.

In the compounds of the invention the presence of a methyl group in the pyridyl moiety plays a fundamental role in potentiating the oral antiallergic activity, as is shown by the following Table, where the potency ratio of one of the compounds of the invention, the 2-trans-[2-(6-methyl-2-pyridyl)-cyclopropyl]-3-propyl-chromone-6-carboxylic acid (K 13804), is reported with respect to the desmethyl analog, 2-trans-[2-(2-pyridyl)-cyclopropyl]-3-propyl-chromone-6-carboxylic acid (FCE 20251), described in our U.S. Pat. No. 4,160,028. The antiallergic activity of the compound FCE 20251 is represented as 1.

TABLE

| Compound | Potency ratio (FCE 20251 = 1) | Fiducial limits for P = 0.95 |
|---|---|---|
| K 13804 | 4.96 | (2.33–9.58) |

The antiallergic activity was determined by the inhibition of the IgE-mediated PCA according to Goose J. and Blair A.M.J.N. (loc.cit.) using homocytotropic antibodies raised in rats following the method of Mota I., Immunology, 7, 681(1964). The tested compounds were administered per os 15 minutes before the administration of the antigen at 3 or more dosage levels. At least 8 rats were used per each dose. The potency ratios were calculated according to the method of Finney, D.J. (1952) Statistical Method in Biological Assay, C. Griffin, London, page 118.

The compounds of the present invention also possess anti-ulcer activity, as demonstrated by the fact that they are active in inhibiting stress-induced ulcers in rats undergoing restraint in a water-bath at 25° C. for 40 minutes, using a modification of the technique of Takagi K. and Okabe S. (Jap. J. of Pharmac., 1968, 19:9).

In view of their high therapeutic index, the compounds of the invention can be used safely in medicine.

For example, the approximate acute toxicity (LD 50) of the compound 2-trans-[2-(6-methyl-2-pyridyl)-cyclopropyl[-3-propyl-chromone-6-carboxylic acid in the mouse, determined by single administration of increasing doses and measured on the seventh day of treatment, is higher than 400 mg/kg per os. Analogous toxicity data have been found for the other compounds of the invention. The compounds of the invention may be administered in a conventional manner, for instance, orally and parenterally at a daily dosage preferably of 0.25 to 15 mg/kg, or by inhalation, preferably at a daily dosage of 0.25 to 100 mg, preferably 0.5 to 25 mg or by topical application.

The invention includes pharmaceutical compositions containing a compound of this invention in association with a pharmaceutically acceptable carrier and/or diluent. The most suitable carrier or diluent will depend upon the desired mode of administration. The compositions may be formulated in the conventional manner with the usual ingredients. For example, the compounds of the invention may be administered in the form of aqueous or oily solutions or suspensions, aerosols, as well as powders, tablets, pills, gelatine capsules, syrups, or creams, or lotions for topical use.

Thus, for oral administration, the pharmaceutical compositions containing the compounds of this invention, are preferably tablets pills or gelatine capsules which contain the active substance together with diluents, such as, for example, lactose, dextrose, sucrose, mannitol, sorbitol, cellulose; lubricants, for instance, silica, talc, stearic acid, magnesium or calcium stearate, and/or polyethylene glycols; or they may also contain binders, such as, for example, starches, gelatine, methylcellulose, carboxymethylcellulose, gum-arabic, tragacanth, polyvinylpyrrolidone, disintegrating agents, such as, for instance, starches, alginic acid, alginates, sodium starch glycolate; effervescing mixtures; dyestuffs; sweeteners, wetting agents, such as, for instance, lecithin, polysorbates, laurylsulphates; and, in general, non-toxic and pharmacologically inactice substances used in pharmaceutical formulations. Said pharmaceutical preparations may be manufactured in known manner, for example, by means of mixing, granulating, tabletting, sugar-coating; or film-coating processes.

For the treatment of alergic asthma, the compounds of the invention are also administered by inhalation. For such use, suitable compositions may comprise a suspension or solution of the active ingredient, preferably in the form of a salt, such as the sodium salt in water, for administration by means of a conventional nebulizer. Alternatively, the compositions may comprise a suspension or a solution of the active ingredient in a conventional liquified propellant, such as, dichlorodifluoromethane or dichlorotetrafluoro ethane to be administered from a pressurized container, i.e. an aerosol dispenser.

When the medicament is not soluble in the propellant, it may be necessary to add a co-solvent, e.g. ethanol, dipropylene glycol, isopropyl myristate, and/or a surface-active agent to the composition, in order to suspend the medicament in the propellant medium and such surface-active agents may be any of those commonly used for this purpose, such as non-ionic surface-active agents, e.g. lecithin.

The compounds of the invention may also be administered in the form of powders by means of a suitable insufflator device and in this case the fine particle sized powders of the active ingredient may be mixed with a diluent material such a lactose.

Furthermore, the compounds of this invention may also be administered by intradermal or intravenous injection in the conventional manner.

In addition to the internal administration, the compounds of this invention may find use in compositions for topical application, e.g: as creams, lotions or pastes for use in dermatological treatments.

For these compositions the active ingredient may be mixed with conventional oleaginous or emulsifying excipients.

The following examples illustrate the present invention.

EXAMPLE 1

Trimethyl-sulphoxonium iodide (3.46 g) was reacted with 50% sodium hydride (0.76 g) in dimethylformamide (50 ml) with stirring at room temperature for 2 hours. A solution of 2-trans-[2-(6-methyl-2-pyridyl)-ethenyl]-3-propyl-chromone-6-carboxylic acid, methyl ester, m.p. 161°–164° C., (3.8 g) in dimethylformamide (50 ml) was added. The mixture was allowed to react with stirring at room temperature for 6 hours, then was diluted with ice water. The precipitate was extracted with ethyl acetate and the solution was evaporated to dryness in vacuo. The 2-trans-[2-(6-methyl-2-pyridyl)-cyclopropyl]-3-propyl-chromone-6-carboxylic acid, methyl ester so obtained (3.9 g) was reacted with 1% KOH in 95% ethanol solution (67.6 ml) at reflux temperature for 10 minutes. After cooling, the reaction mixture was diluted with ice water, neutralized with NaHPO$_4$ and the precipitate was filtered and washed with water until neutral. Crystallization from 2-butanone yielded 1.4 g of 2-trans-[2-(6-methyl-2-pyridyl)-cyclopropyl]-3-propyl-chromone-6-carboxylic acid, m.p. 216°–217° C.; IR (KBr): γ(C═O) acid 1710 cm$^{-1}$, γ(C═O) chromone 1640, 1620 cm$^{-1}$; NMR (DMSO d6) γ: 0.82 (t) (—CH$_2$CH$_2$CH$_3$); 1.44 (m) (—CH$_2$CH$_2$CH$_3$), 1.85 (m)

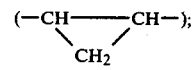

2.47 (s) (—CH$_3$); 2.40–3.04 (m) (—CH$_2$CH$_2$CH$_3$ and

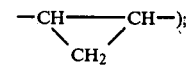

7.07–7.78 (m) (pyridyl protons); 7.69 (d) (C-8 chromonyl proton); 8.28 (d.d) (C-7 chromonyl proton); 8.64 (d) (C-5 chromonyl proton).

By proceeding analogously the following compounds were prepared: 2-trans-[2-(6-methyl-2-pyridyl)-cyclopropyl]-3-ethoxy-chromone-6-carboxylic acid, m.p. 229°–230° C., 2-trans-[2-(6-methyl-2-pyridyl)-cyclopropyl]-3-propoxy-chromone-6-carboxylic acid, m.p. 199°–200° C.; 2-trans-[2-(6-methyl-2-pyridyl)-cyclopropyl]-3-allyloxy-chromone-6-carboxylic-acid, m.p., 180°–181° C.; 2-trans-[2-(5-methyl-2-pyridyl)-cyclopropyl]-3-propyl-chromone-6-carboxylic acid, m.p. 206°–207° C.; 2-trans-[2-(5-methyl-2-pyridyl)-cyclopropyl]-3-ethoxy-chromone-6-carboxylic acid, m.p. 207°–208° C., 2-trans-[2-(6-methyl-2-pyridyl)-cyclopropyl]-3-ethyl-chromone-6-carboxylic acid, m.p. 291°–292° C.

EXAMPLE 2

Trimethylsulphoxonium iodide (1.95 g) was reacted with 50% sodium hydride (0.42 g) in dimethylformamide (25 ml) with stirring at room temperature for 2 hours. A solution of 2-trans-[2-(5-methyl-2-pyridyl)-ethenyl]-3-propoxy-chromone-6-carboxylic acid, tert-butyl ester (3.15 g) in dimethylformamide (25 ml) was then added. The mixture was allowed to react with stirring at room temperature for 6 hours and was then diluted with ice water and extracted with ethyl acetate, The organic layer was washed with water until neutral and then evaporated to dryness in vacuo. The crude product (2.7 g) was purified through a SiO$_2$ column using chloroform as eluant, so obtaining 2.05 g of 2-trans-[2-(5-methyl-2-pyridyl)-cyclopropyl]-3-propoxy-chromone-6-carboxylic acid, tert-butyl ester which was reacted with trimethylsilyl iodide (1 g=1.2 ml) in C Cl$_4$ (30 ml) under nitrogen, with stirring at room temperature for 4 hours and then at 50° C. for 2 hours. After cooling, the reaction mixture was diluted with ethyl ether and extracted with 2% aqueous NaHCO$_3$. The aqueous layer was separated and acidified with NaH$_2$PO$_4$ and the precipitate was filtered off and washed with water until neutral.

Crystallization from ethanol gave 1.25 g of 2-trans-[2-(5-methyl-2-pyridyl)-cyclopropyl]-3-propoxy-chromone-6-carboxylic acid, m.p. 201°–202° C.; NMR (DMSO d6)δ: 0.84 (t) (—OCH$_2$CH$_2$CH$_3$); 1.60 (m) (—OCH$_2$—CH$_2$—CH$_3$); 1.88 (m)

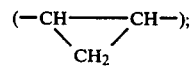

2.30 (S) (—CH$_3$); 2.95 (m)

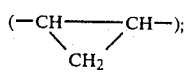

4.00 (m)(—O$\underline{CH_2}$—CH$_2$—CH$_3$); 7.41 (d) (C-3 pyridyl proton); 7.61 (d.d) (C-4 pyridyl proton); 7.73 (d) (C-8 chromonyl proton); 8.30 (d.d) (C-7 chromonyl proton); 8.42 (d) (C-6 pyridyl proton); 8.66 (d) (C-5 chromonyl proton).

EXAMPLE 3

2-trans-[2-(6-methyl-2-pyridyl)-cyclopropyl]-3-propyl-chromone-6-carboxylic acid (0.6 g) was reacted with ethyl iodide (0.54 g) and anhydrous K$_2$CO$_3$ (0.63 g) in dimethylformamide (7 ml) with stirring at room temperature for 6 hours. After dilution with ice water the precipitate was filtered off and crystallized from n-hexane to yield 0.4 g of 2-trans[2-(6-methyl-2-pyridyl)-cyclopropyl]-3-propyl-chromone-6-carboxylic acid, ethyl ester, m.p. 95°–97° C. By proceeding analogously the 2-trans-[2-(6-methyl-2-pyridyl)cyclopropyl]-3-ethoxy-chromone-6-carboxylic acid, methyl ester (m.p. 94°–97° C.) was obtained.

EXAMPLE 4

2-trans-[2-(6-methyl-2-pyridyl)-cyclopropyl]-3-propyl-chromone-6-carboxylic acid (1.3 g) was reacted with SOCl$_2$ (0.6 ml) in dioxane (30 ml) at reflux temperature for 1 hour. The reaction mixture was then evaporated to dryness in vacuo. The residue was dissolved in anhydrous dioxane (30 ml) containing triethylamine (0.5 ml) and reacted with 2-diethylamino-ethanol (1 ml) at room temperature for 24 hours. After dilution with water the precipitate was extracted with ethyl acetate and the solution was evaporated to dryness in vacuo. The residue was purified using a silica gel column and benzene-ethylacetate as eluent: 0.4 g of 2-trans-[2-(6-methyl-2-pyridyl)-cyclopropyl]-3-propyl-chromone-6-carboxylic acid, 2-diethylaminoethyl ester, oil, were obtained. NMR (CDCl$_3$)δ: 0.90 (t) (—CH$_2$—CH$_2$—$\underline{CH_3}$); 1.10 )t)

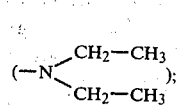

1.55 (m) (—CH$_2$—$\underline{CH_2}$—CH$_3$); 1.87 (m)

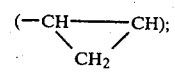

2.52 (s) (—CH$_3$); 2.71 (q)

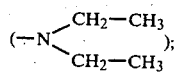

2.50–2.90 (m) (—$\underline{CH_2}$—CH$_2$—CH$_3$ and

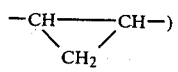

2.95 (t)

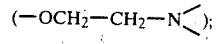

4.49 (t)

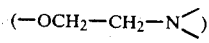

6.96–7.64 (m) (pyridyl protons); 7.47 (d) (C-8 chromonyl proton); 8.32 (d.d) (C-7 chromonyl proton); 8.93 (d) (C-5 chromonyl proton).

By proceeding analogously the 2-trans-[2-(6-methyl-2-pyridyl)-cyclopropyl]-3-ethoxy-chromone-6-carboxylic acid, 2-diethylaminoethyl ester was prepared.

EXAMPLE 5

2-trans-[2-(6-methyl-2-pyridyl)-cyclopropyl]-3-propyl-chromone-6-carboxylic acid was dissolved in the stoichiometric amount of 2 N NaOH. The solution was then concentrated in vacuo and diluted with acetone. The precipitate was filtered off and washed with acetone. The 2-trans-[2-(6-methyl-2-pyridyl)-cyclopropyl]-3-propyl-chromone-6-carboxylic acid, sodium salt, m.p. >300° C., was obtained.

EXAMPLE 6

Tablets, each weighing 150 mg and containing 50 mg of the active substance are manufactured as follows:

| Composition (for 10,000 tablets) | |
|---|---|
| 2-trans-[2-(6-methyl-2-pyridyl)-cyclopropyl]-3-propyl-chromone-6-carboxylic acid | 500 g |
| lactose | 710 g |
| corn starch | 237.5 g |
| talc powder | 37.5 g |
| magnesium stearate | 15 g |

The 2-trans-[2-(6-methyl-2-pyridyl)-cyclopropyl]-3-propyl-chromone-6-carboxylic acid, lactose and half the corn starch are mixed. The mixture is then forced through a sieve having 0.5 mm openings. Corn starch (18 g) is suspended in warm water (180 ml).

The resulting past is used to granulate the powder.

The granules are dried and comminuted on a sieve having 1.4 mm openings. The remaining starch, talc and magnesium stearate are added, carefully mixed and processed into tablets using punches of 8 mm diameter.

EXAMPLE 7

| Aerosol formulation | |
|---|---|
| 2-trans-[2-(6-methyl-2-pyridyl)-cyclopropyl]-3-propyl-chromone-6-carboxylic acid | 2% |
| ethanol | 10% |
| lecithin | 0.2% |
| mixture of dichlorodifluoromethane and dichlorotetrafluoromethane (70:30 mixture) ad | 100% |

We claim:

1. 2-(Pyridyl-cyclopropyl)chromone derivative of the formula (I)

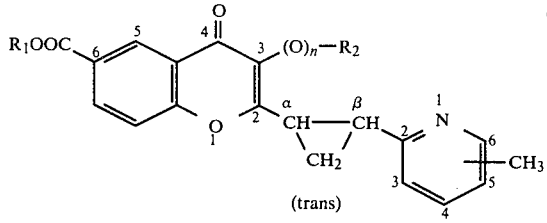

wherein n is 0 or 1;

$R_1$ represents a hydrogen atom or a $C_1$–$C_4$ alkyl group which is unsubstituted or substituted by a

group, wherein each of $R_3$ and $R_4$ independently represents a hydrogen atom or a $C_1$ or $C_2$ alkyl group, thereby providing a basic ester group; $R_2$ represents a $C_2$ or $C_3$ alkyl group or an allyl group, and wherein the methyl group on the pyridine ring is in the 6- or in the 5-position, and pharmaceutically acceptable salts thereof.

2. A 2-(Pyridyl-cyclopropyl)chromone derivative selected from:

2-trans-[2-(6-methyl-2-pyridyl)-cyclopropyl]-3-propyl-chromone-6-carboxylic-acid;

2-trans-[2-(6-methyl-2-pyridyl)-cyclopropyl]-3-propoxy-chromone-6-carboxylic-acid;

2-trans-[2-(6-methyl-2-pyridyl)-cyclopropyl]-3-ethoxy-chromone-6-carboxylic-acid;

2-trans-[2-(6-methyl-2-pyridyl)-cyclopropyl]-3-allyloxy-chromone-6-carboxylic-acid; and 2-trans-[2-(5-methyl-2-pyridyl)-cyclopropyl]-3-propyl-chromone-6-carboxylic-acid, as well as the pharmaceutically acceptable salts, the $C_1$–$C_4$ alkyl, 2-dimethylaminoethyl and 2-diethylaminoethyl esters thereof, and the pharmaceutically acceptable salts of the 2-dimethylaminoethyl and 2-diethylaminoethyl esters.

3. Derivative of claim 1, wherein said derivative has the methyl group on the pyridyl ring located in the 6-position of the pyridyl ring.

4. The compound 2-trans-[2-(6-methyl-2-pyridyl)cyclopropyl]-3-propyl-chromone-6-carboxylic acid.

5. A derivative according to claim 1, 2, 3 or 4 in the form of a sodium salt or potassium salt.

6. A derivative according to claim 1, 2, 3 or 4 in the form of the hydrochloride of a basic ester.

7. A derivative according to claim 1, 2, 3 or 4 in the form of a 2-dimethylamino ethyl or 2-diethylamino ethyl ester.

8. A derivative according to claim 1, 2, 3 or 4 in the form of a methyl or ethyl ester.

9. A method of treating allergies in a patient in need of such treatment, said method comprising administering to said patient an anti-allergic amount of a compound of any one of claims 1, 3 or 4.

10. A pharmaceutical composition suitable for the treatment of allergies, said composition comprising a compound of any one of claims 1, 2, 3 or 4 and a pharmaceutically acceptable carrier.

11. Composition according to claim 10 in the form of tablets, pills, capsules or a liquid for inhalation.

12. Composition according to claim 10 in the form of an aerosol.

* * * * *